US005451603A

United States Patent [19]
Piggott

[11] Patent Number: 5,451,603
[45] Date of Patent: Sep. 19, 1995

[54] 3,4-DIARYLCHROMANS FOR TREATMENT OF DERMATITIS

[75] Inventor: James R. Piggott, Bothell, Wash.

[73] Assignee: ZymoGenetics, Inc., Seattle, Wash.

[21] Appl. No.: 29,739

[22] Filed: Mar. 11, 1993

[51] Int. Cl.⁶ .................... A61K 31/35; A61K 31/40
[52] U.S. Cl. ........................ 514/422; 514/456
[58] Field of Search .................. 514/456, 422

[56] References Cited

U.S. PATENT DOCUMENTS

| | | | |
|---|---|---|---|
| 3,340,276 | 9/1967 | Carney et al. | 260/345.2 |
| 3,822,287 | 7/1974 | Bolger et al. | 260/326.5 |
| 4,362,742 | 12/1982 | Sullivan | 514/456 |
| 4,447,622 | 5/1984 | Salman et al. | 548/525 |
| 4,742,066 | 5/1988 | Deckner et al. | 514/311 |
| 4,851,433 | 7/1989 | Kraus | 514/648 |
| 5,015,661 | 5/1991 | Walser | 514/443 |
| 5,248,777 | 9/1993 | Chandraratna | 546/165 |
| 5,298,512 | 3/1994 | Eggler et al. | 514/314 |

FOREIGN PATENT DOCUMENTS

| | | |
|---|---|---|
| 92/06084 | 4/1992 | WIPO. |
| 92/18481 | 10/1992 | WIPO. |
| 92/20642 | 11/1992 | WIPO. |
| 93/20058 | 10/1993 | WIPO. |
| 93/20059 | 10/1993 | WIPO. |

OTHER PUBLICATIONS

Srivastava, *Agents and Actions* 18: 596–599, 1986.
Veigl et al., *Pharmac, Ther.* 44: 181–239, 1988.
Beitner et al., *Gen. Pharmac.* 20: 641–646, 1989.
Wiseman, *Trends in Pharmacol. Sci.* 15: 88–89, 1994.
Beattie et al., *Cancer Res.* 51: 2025–2028, 1991.
Kanitakis et al., *J. Cutan, Pathol.* 16: 272–276, 1989.
MacLean et al., *J. Reprod. Med.* 35: 1015–1016, 1990.
Salman et al., *J. Med. Chem.* 29: 1801–1803, 1986.
Barrera et al., *Biochemical Pharmacol.* 35: 2984–2986, 1986.
Misra et al., *Int. J. Cancer* 43: 781–783, 1989.
Dhawan et al., *Br. J. Pharmacol.* 49: 64–73, 1973.
Mac Neil et al., *Br. J. Dermatol.* 128: 143–150, 1993.
Saeed et al., *Biochem. Biophys. Res. Comm.* 125: 346-352, 1984.
Ray et al., *J. Med. Chem.* 19: 276–279, 1976.
Salman et al., *J. Med. Chem.* 26: 592–595, 1983.

*Primary Examiner*—Raymond Henley, III
*Assistant Examiner*—Phyllis G. Spivack
*Attorney, Agent, or Firm*—Gary E. Parker; Deborah A. Sawislak; Debra K. Leith

[57] ABSTRACT

Methods for the treatment of dermatitis are disclosed wherein 3,4-diarylchromans and their pharmaceutically acceptable salts are formulated into medicaments, including oral and topical medicaments, and are administered to a patient suffering from dermatitis.

15 Claims, No Drawings

3,4-DIARYLCHROMANS FOR TREATMENT OF DERMATITIS

BACKGROUND OF THE INVENTION

Dermatitis encompasses a number of conditions characterized by reddish skin lesions that can develop into scaly, thickened plaques. These lesions can arise from any of several primary causes, including contact with allergens, ultraviolet light or chemicals, systemically administered drugs, or localized trauma (irritation). The causes of certain forms of dermatitis are unknown.

Eczematous dermatitis refers to a group of conditions characterized in the initial stages by edematous, oozing plaques that often contain blisters. These lesions are prone to bacterial infection. Fluid leaks into the intercellular spaces in the epidermis, giving it a spongy appearance. Over time, oozing diminishes, and the lesions become scaly as the epidermis thickens (epidermal hyperplasia).

Of particular concern are chronic forms of dermatitis, including psoriasis and the chronic stages of eczematous dermatitis. Psoriasis is characterized by round, thick, dry, reddish patches covered with silvery scales. Psoriasis may be localized or generalized, and in the latter case may become life-threatening. Psoriatic lesions show marked epidermal hyperplasia and hyperproliferation of keratinocytes. The etiology of psoriasis is believed to include hereditary and autoimmune components. Chronic lesions of eczematous dermatitis are clinically and histologically similar to psoriatic plaques.

Cellular proliferation (e.g. proliferation of keratinocytes) is regulated in part by intracellular calcium levels. Changes in intracellular calcium concentrations influence the phosphorylation of proteins, thus influencing proliferation and other cellular processes. One of the molecules that mediates the effect of intracellular calcium levels on protein phosphorylation is calmodulin, a protein co-factor for protein kinase C.

Psoriasis is treated by the application of corticosteroids, coal tar ointments, or anthralin. These treatments are only partially effective and may merely contain, not reverse, the disease. Anthralin may cause irritation, and its safety in children and pregnant women has not been established. Corticosteroids have a number of undesirable side effects, including edema and mineral imbalances. Non-steroidal anti-inflammatory agents are generally not effective.

There remains a need in the art for treatments for dermatitis that are effective and lack serious side effects. The present invention addresses this need and provides other, related advantages.

Disclosure of the Invention

Broadly stated, the present invention is directed to methods for treating dermatitis (including psoriasis), including the chronic stages of these conditions, which are characterized by the hyperproliferation of keratinocytes. The present invention makes use of compounds of the formula (I):

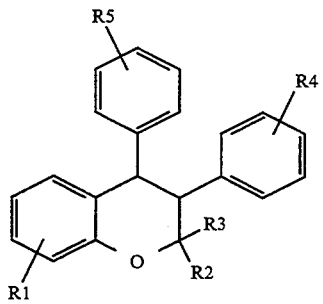

and pharmaceutically acceptable salts thereof, wherein R1, R4 and R5 are individually hydrogen, hydroxy, halo, trifluoromethyl, lower alkyl, lower alkoxy or tertiary amino lower alkoxy; and R2 and R3 are individually hydrogen or lower alkyl.

Within one aspect, the present invention provides a method for treating eczematous dermatitis comprising administering to a patient suffering from eczematous dermatitis an effective amount of a composition comprising a compound of formula (I) or a pharmaceutically acceptable salt thereof in combination with a pharmaceutically acceptable carrier.

Within a related aspect, the present invention provides a method for treating psoriasis comprising administering to a patient a composition comprising a compound of formula (I) or a pharmaceutically acceptable salt thereof as described above.

Within another aspect, the present invention provides a method for inhibiting the proliferation of keratinocytes in a patient. Briefly, a compound of formula (I) or a pharmaceutically acceptable salt thereof in combination with a pharmaceutically acceptable carrier is administered to a patient in an amount sufficient to inhibit keratinocyte proliferation.

Yet another aspect of the present invention provides a method for inhibiting calmodulin activity in a patient comprising administering to the patient a compound of formula (I) or a pharmaceutically acceptable salt thereof in combination with a pharmaceutically acceptable carrier in an amount sufficient to inhibit calmodulin activity.

These and other aspects of the invention will become evident upon reference to the following detailed description.

DETAILED DESCRIPTION OF THE INVENTION

According to the present invention, 3,4-diarylchromans, such as centchroman (3,4-trans-2,2-dimethyl-3-phenyl-4-[p-(beta-pyrrolidinoethoxy)phenyl]-7-methoxy-chroman), are used for the treatment of dermatitis, including eczematous dermatitis and psoriasis. Centchroman has very low toxicity and can be administered chronically. The 3,4-diarylchromans are represented by the structure

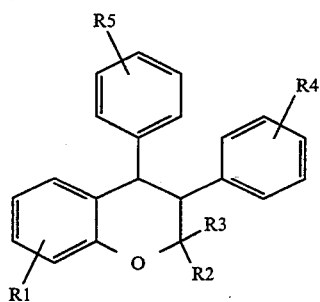 (I)

Within formula (I), R1, R4 and R5 are individually hydrogen, halo, trifluoromethyl, lower alkyl, lower alkoxy or tertiary amino lower alkoxy; and R2 and R3 are individually H or a lower alkyl. As used herein, the term "lower alkyl" includes straight and branched chain alkyl radicals containing from 1 to 6 carbon atoms, such as methyl, ethyl, n-propyl, isopropyl, n-butyl, tert-butyl, n-amyl, sec-amyl, n-hexyl, 2-ethylbutyl, 2,3-dimethylbutyl and the like. The term "lower alkoxy" includes straight and branched chain alkoxy radicals containing from 1 to 6 carbon atoms, such as methoxy, ethoxy, n-propoxy, isopropoxy, n-butoxy, tert-butoxy, n-amyloxy, sec-amyloxy, n-hexyloxy, 2-ethyl-butoxy, 2,3-dimethylbutoxy and the like. "Halo" includes chloro, fluoro, bromo and iodo. The tertiary amino radical may be a dialkylamine such as a dimethyl, diethyl, dipropyl, dibutyl or polymethyleneimine, e.g. piperidine, pyrrolidine, N-methyl piperazine or morpholine. Preferred compounds include those in which R1 is lower alkoxy; R2 and R3 are lower alkyl, especially methyl; R4 is H; and R5 is tertiary amino lower alkoxy of the polyethyleneimine type. Within particularly preferred embodiments, R1 is in the 7-position and is lower alkoxy, particularly methoxy; each of R2 and R3 is methyl, R4 is H and R5 is in the 4-position and is a tertiary amino lower alkoxy radical such as pyrrolidinoethoxy.

It is preferred to use the compounds of structure (I) in the trans configuration. The l enantiomeric forms are preferred over racemic mixtures.

A particularly preferred compound for use within the present invention is centchroman (II):

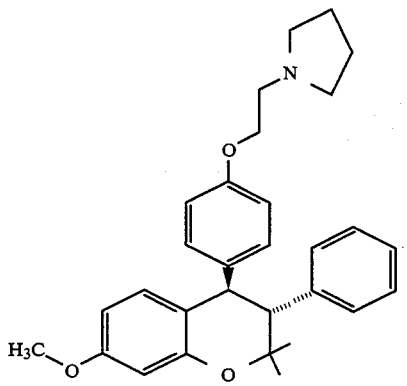 (II)

3,4-diarylchromans are prepared according to known methods, such as those disclosed in U.S. Pat. No. 3,340,276 to Carney et al., U.S. Pat. No. 3,822,287 to Bolger, and Ray et al., *J. Med. Chem.* 19:276–279, 1976, which are incorporated herein by reference. Conversion of the cis to the trans configuration by means of an organometallic base-catalyzed rearrangement is disclosed in U.S. Pat. No. 3,822,287. The optically active d- and l-enantiomers may be prepared as disclosed by Salman et al. in U.S. Pat. No. 4,447,622 (incorporated herein by reference) by forming an optically active acid salt which is subjected to alkaline hydrolysis to produce the desired enantiomer.

Within the present invention, 3,4-diarylchromans may be prepared in the form of pharmaceutically acceptable salts, especially acid-addition salts, including salts of organic acids and mineral acids. Examples of such salts include organic acids such as formic acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulfuric and phosphoric acids and the like. The acid addition salts may be obtained as the direct products of compound synthesis. In the alternative, the free base may be dissolved in a suitable solvent containing the appropriate acid, and the salt isolated by evaporating the the solvent or otherwise separating the salt and solvent.

According to the present invention, the 3,4-diarylchromans and their salts are used within human and veterinary medicine for the treatment of eczematous dermatitis and psoriasis. "Eczematous dermatitis" includes allergic contact dermatitis, atopic dermatitis, photoeczematous dermatitis and primary irritant dermatitis. The methods of the present invention may be used to treat these conditions in their acute or chronic stages. While not wishing to be bound by theory, it is believed that the therapeutic effect of the 3,4-diarylchromans is at least in part due to an antagonistic effect on calmodulin, making these compounds particularly effective in the chronic, hyperproliferative stages of eczematous dermatitis and psoriasis.

For use within the present invention, 3,4-diarylchromans and their pharmaceutically acceptable salts are formulated with a pharmaceutically acceptable carrier to provide a medicament for topical or oral administration according to conventional methods. Formulations may further include one or more diluents, fillers, emulsifiers, preservatives, buffers, excipients, etc. and may be provided in such forms as liquids, ointments, salves, gels, emulsions and the like. One skilled in this art may formulate the compounds in an appropriate manner, and in accordance with accepted practices, such as those disclosed in *Remington's Pharmaceutical Sciences,* 18th ed., Gennaro, ed., Mack Publishing Co., Easton, Pa., 1990 (which is incorporated herein by reference in its entirety.) Such compositions may further include one or more auxiliary substances, such as wetting agents, stabilizers, coloring, penetration enhancers, etc.

Within a preferred embodiment, pharmaceutical compositions are applied topically to skin lesions. Suitable compositions in this regard include oil-based formulations such as ointments, water-in-oil emulsions and solutions of the active agent in a volatile solvent such as an ethanol/ether mixture. Compositions of this type are applied from one to several times daily. Water-based formulations may be applied as wet dressings.

The pharmaceutical compositions may also be administered orally, preferably as tablets or capsules. Oral administration will generally take place at daily to weekly intervals.

An "effective amount" of such a pharmaceutical composition is the amount that provides a clinically significant improvement in the symptoms of the condition to be treated. In particular, it is desirable to achieve a reduction in epidermal hyperplasia and/or keratinocyte hyperproliferation. Determination of such amounts will generally be done empirically and is within the ordinary level of skill in the art. The treatment may be adjusted as necessary to obtain the desired effects, such as by altering the concentration of active ingredient in the formulation or by varying the treatment schedule. The actual amount administered will of course depend in part on the particular condition to be treated (including its extent and severity), age, weight, and general health of the patient, and other factors evident to those skilled in the art. For example, a typical formulation for topical delivery will contain from 0.01 to 10 weight percent of a 3,4-diarylchroman in a suitable vehicle, more preferably from 0.5 to 5 weight percent. The formulation will be applied to the affected skin from one to several times per day until the desired improvement is achieved.

General guidance for treatment regimens is obtained from experiments carried out in animal models of the disease of interest. For example, animal models of psoriasis include the analysis of histological alterations in adult mouse tail epidermis (Hofbauer et al, *Brit. J. Dermatol.* 118: 85–89, 1988; Bladon et al., *Arch Dermatol. Res.* 277: 121–125, 1985, incorporated herein by reference). In this model, anti-psoriatic activity is indicated by the induction of a granular layer and orthokeratosis in areas of scale between the hinges of the tail epidermis. Typically, a topical ointment is applied daily for seven consecutive days, then sacrificed, and tail skin is examined histologically. An additional model is provided by grafting psoriatic human skin to congenitally athymic (nude) mice (Krueger et al., *J. Invest. Dermatol.* 64:307–312, 1975, incorporated herein by reference). Such grafts have been shown to retain the characteristic histology for up to eleven weeks. As in the mouse tail model, the test composition is applied to the skin at predetermined intervals for a period of one to several weeks, at which time the animals are sacrificed and the skin grafts examined histologically. A third model has been disclosed by Fretland et al. (*Inflammation* 14: 727–739, 1990; incorporated herein by reference). Briefly, inflammation is induced in guinea pig epidermis by topically applying phorbol ester (phorbol-12-myristate-13-acetate; PMA), typically at ca. 2 g/ml in acetone, to one ear and vehicle to the contralateral ear. Test compounds are applied concurrently with the PMA, or may be given orally. Histological analysis is performed at 96 hours after application of PMA. This model duplicates many symptoms of human psoriasis, including edema, inflammatory cell diapedesis and infiltration, high $LTB_4$ levels and epidermal proliferation.

Calmodulin activity is conveniently assayed by measuring the activity of calmodulin-dependent enzymes. See, for example, Blumenthal et al., *Biochem. Biophys. Res. Comm.* 156: 860–865, 1988, which is incorporated herein by reference. Calmodulin-dependent enzymes include phosphorylase kinase, brain multifunctional calmodulin-dependent protein kinase and calmodulin-dependent protein phosphatase (calcineurin). Phosphorylase kinase activity is determined by measuring rates of $^{32}P$ incorporation into phosphorylase b using a filter paper assay (Roskoski, *Methods Enzymol.* 99: 3–6, 1983, incorporated herein by reference). A reaction mixture containing 50 mM magnesium acetate, 200 μM $CaCl_2$, 5 mg/ml phosphorylase b, 0.9 μg/ml skeletal muscle phosphorylase kinase, calmodulin, and the test compound are combined. The mixture is incubated at 30° C. for five minutes, and the reaction is initiated by the addition of [γ-$^{32}$P]ATP. Phosphatase activity is assayed by determining rates of $^{32}Pi$ release from a synthetic phosphopeptide corresponding to residues 81–99 of bovine cardiac cAMP-dependent protein kinase regulatory subunit. The reaction mixture contains 50 mM MOPS (4-morpholinepropanesulfonic acid) pH 7.0, 15 mM 2-mercaptoethanol, 2 mM magnesium acetate, 2 mM $MnCl_2$, 0.3 μg/ml bovine brain calmodulin-dependent phosphatase, calmodulin, and the test compound. The mixture is incubated at 30° C. for five minutes, and the reaction is initiated by the addition of $^{32}$P-labeled peptide. Protein kinase activity may be assayed by determining the rate of $^{32}P$ incorporation into chicken gizzard muscle myosin light chain using a filter paper method (Roskoski, ibid.) in a reaction mixture of 50 mM Tris, pH 7.6, 0.6 mM dithiothreitol, 0.6 mg/ml bovine serum albumin (BSA), 80 mM NaCl, 0.5 mM $CaCl_2$, 1.0 μg/ml kinase, calmodulin and test compound. The reaction is initiated by the addition of Mg-[γ-$^{32}$P]ATP and myosin light chain (40 μM final concentration) at 25° C. Calmodulin concentrations typically range between 1 nM and 1 μM.

The following examples are offered by way of illustration, not limitation.

Example 1

Collodion solvent is added to pure centchroman to provide a final concentration of 100 mg centchroman per 10 ml of solvent. The solvent is a mixture of three parts by volume of diethyl ether to one part by volume of ethanol. The resulting solution is aliquotted into sterile dropper bottles. For use, the formulation is applied directly to affected skin using a dropper in an amount sufficient to cover the affected area.

Example 2

Soft white paraffin BP is heated to 60° C., at which point it melts. Centchroman is added directly at a concentration of 10 mg per gram of paraffin, and the mixture is thoroughly stirred. After cooling, the formulation is packaged in sterile containers. For use, the formulation is applied by rubbing directly onto affected skin.

Although the foregoing invention has been described in some detail by way of illustration and example for purposes of clarity of understanding, it will be evident that certain changes and modifications may be practiced within the scope of the appended claims.

I claim:

1. A method for treating dermatitis in a patient comprising administering to a patient suffering from dermatitis an effective amount of a composition comprising a compound of the formula

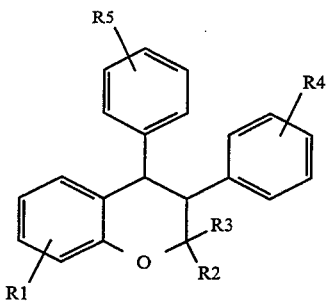

or a pharmaceutically acceptable salt thereof, wherein:
R1, R4 and R5 are individually hydrogen, hydroxy, halo, trifluoromethyl, lower alkyl, lower alkoxy or tertiary amino lower alkoxy; and
R2 and R3 are individually hydrogen or lower alkyl,
in combination with a pharmaceutically acceptable carrier, wherein said dermatitis is psoriasis, atopic dermatitis, photoeczematous dermatitis, primary irritant dermatitis or allergic contact dermatitis.

2. A method according to claim 1 wherein R1 is lower alkoxy, R2 and R3 are lower alkyl, R4 is hydrogen and R5 is tertiary amino lower alkoxy.

3. A method according to claim 1 wherein R1 is methoxy.

4. A method according to claim 1 wherein R2 and R3 are methyl.

5. A method according to claim 1 wherein R4 is hydrogen.

6. A method according to claim 1 wherein R5 is

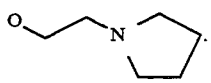

7. A method according to claim 1 wherein said compound is

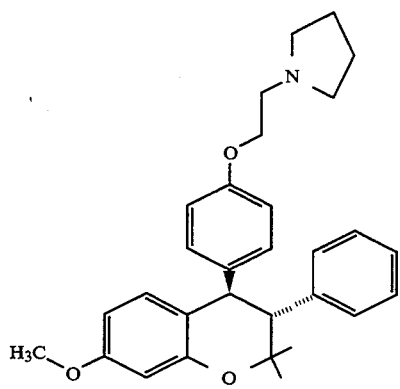

8. A method according to claim 1 wherein said dermatitis is psoriasis.

9. A method according to claim 1 wherein said dermatitis is atopic dermatitis, photoeczematous dermatitis, primary irritant dermatitis or allergic contact dermatitis.

10. A method according to claim 1 wherein said composition is in a form suitable for topical administration.

11. A method for inhibiting hyperproliferation of keratinocytes in a patient comprising administering to a patient a compound of the formula

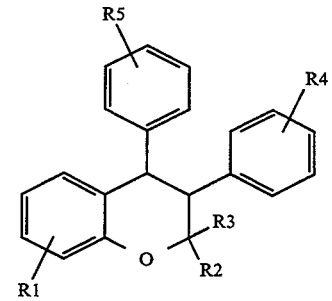

or a pharmaceutically acceptable salt thereof, wherein:
R1, R4 and R5 are individually hydrogen, hydroxy, halo, trifluoromethyl, lower alkyl, lower alkoxy or tertiary amino lower alkoxy; and
R2 and R3 are individually hydrogen or lower alkyl,
in combination with a pharmaceutically acceptable carrier, in an amount sufficient to inhibit keratinocyte proliferation.

12. A method according to claim 11 wherein R1 is lower alkoxy, R2 and R3 are lower alkyl, R4 is hydrogen and R5 is tertiary amino lower alkoxy.

13. A method according to claim 11 wherein R1 is methoxy, R2 and R3 are methyl, R4 is hydrogen and R5 is

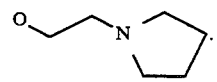

14. A method according to claim 11 wherein said compound is

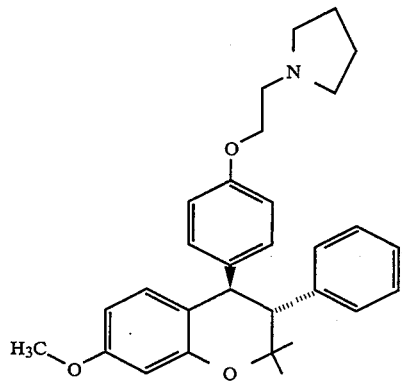

15. A method according to claim 11 wherein said compound is applied topically.

* * * * *